(12) United States Patent
Gianchandani et al.

(10) Patent No.: US 10,132,783 B2
(45) Date of Patent: Nov. 20, 2018

(54) INTEGRATED FLUIDIC SYSTEM FOR GAS CHROMATOGRAPHY

(71) Applicant: THE REGENTS OF THE UNIVERSITY OF MICHIGAN, Ann Arbor, MI (US)

(72) Inventors: Yogesh B. Gianchandani, Ann Arbor, MI (US); Yutao Qin, Ann Arbor, MI (US)

(73) Assignee: The Regents of The University of Michigan, Ann Arbor, MI (US)

( * ) Notice: Subject to any disclaimer, the term of this patent is extended or adjusted under 35 U.S.C. 154(b) by 218 days.

(21) Appl. No.: 14/890,771

(22) PCT Filed: May 16, 2014

(86) PCT No.: PCT/US2014/038421
§ 371 (c)(1),
(2) Date: Nov. 12, 2015

(87) PCT Pub. No.: WO2014/186720
PCT Pub. Date: Nov. 20, 2014

(65) Prior Publication Data
US 2016/0103104 A1    Apr. 14, 2016

Related U.S. Application Data

(60) Provisional application No. 61/824,573, filed on May 17, 2013.

(51) Int. Cl.
*G01N 30/60*        (2006.01)
*B01L 3/00*         (2006.01)
(Continued)

(52) U.S. Cl.
CPC .... *G01N 30/6095* (2013.01); *B01L 3/502707* (2013.01); *G01N 30/08* (2013.01);
(Continued)

(58) Field of Classification Search
None
See application file for complete search history.

(56) References Cited

U.S. PATENT DOCUMENTS 5,888,390 A * 3/1999 Craig ............... B01L 3/502707
                                            204/451
6,838,640 B2 * 1/2005 Wise ..................... G01N 30/30
                                            219/201
(Continued)

FOREIGN PATENT DOCUMENTS

WO    WO-2008067296 A2    6/2008
WO    WO-2011050285 A1    4/2011

OTHER PUBLICATIONS

Jing Liu et al: "Demonstration of motionless Knudsen pump based micro-gas chromatography featuring micro-fabricated columns and on-column dectectors", Lab on a Chip, vol. 11, No. 20, Jan. 1, 2011(Jan. 1, 2011), pp. 3487-3492.
(Continued)

*Primary Examiner* — Paul West
*Assistant Examiner* — Mark A Shabman
(74) *Attorney, Agent, or Firm* — Harness, Dickey & Pierce, P.L.C.

(57) ABSTRACT

A method is presented for fabricating a fluidic system for a gas chromatograph. The method includes: microfabricating a portion of a fluidic system of a gas chromatograph on a substrate using a first mask; microfabricating a portion of the fluidic system of the gas chromatograph using a second mask; and microfabricating a portion of the fluidic system of the gas chromatograph using a third mask, such that the first mask, the second mask and the third mask are different from each other and the microfabricating of the fluidic system of the gas chromatograph is completed using only the first, second and third masks. A gas chromatograph wherein a microfabricated Knudsen pump is arranged to operate in a
(Continued)

first direction to draw carrier gas into a preconcentrator and in a second direction to draw gas out of the preconcentrator.

24 Claims, 13 Drawing Sheets

(51) Int. Cl.
    *G01N 30/32*     (2006.01)
    *G01N 30/88*     (2006.01)
    *G01N 30/02*     (2006.01)
    *G01N 30/08*     (2006.01)

(52) U.S. Cl.
    CPC ............. *G01N 30/32* (2013.01); *G01N 30/88* (2013.01); *B01L 2200/12* (2013.01); *B01L 2300/0887* (2013.01); *G01N 2030/025* (2013.01); *G01N 2030/085* (2013.01); *G01N 2030/326* (2013.01); *G01N 2030/328* (2013.01); *G01N 2030/8881* (2013.01)

(56) References Cited

U.S. PATENT DOCUMENTS

| | | | | |
|---|---|---|---|---|
| 7,078,237 B1* | 7/2006 | Mowry | ................. | G01N 31/12 250/288 |
| 7,399,449 B1* | 7/2008 | Oborny | ............. | G01N 33/0006 422/504 |
| 7,530,257 B2* | 5/2009 | Bonne | .................. | B82Y 15/00 73/23.25 |
| 2003/0118481 A1* | 6/2003 | Briscoe | ................ | F04B 19/006 422/89 |
| 2003/0231967 A1* | 12/2003 | Najafi | .................. | F04B 43/043 417/322 |
| 2009/0150087 A1* | 6/2009 | Steinecker | .......... | G01N 30/461 702/24 |
| 2009/0178563 A1* | 7/2009 | Masel | ............... | G01N 30/6095 96/101 |
| 2009/0272270 A1* | 11/2009 | McGill | ................. | B01J 20/205 96/101 |
| 2010/0101411 A1* | 4/2010 | Tipler | ................... | G01N 30/20 95/86 |
| 2012/0207625 A1* | 8/2012 | McNamara | ............ | F04B 19/24 417/207 |
| 2013/0125620 A1* | 5/2013 | Ovadia | ................. | G01N 30/08 73/23.39 |
| 2014/0298990 A1* | 10/2014 | Fan | ..................... | G01N 30/463 95/23 |

OTHER PUBLICATIONS

Klemp M A et al: "Cryofocusing Inlet With Reverse Flow Sample Collection for Gas Chromatography", Analytical Chemistry, American Chemical Society, US, vol. 65, No. 18, Sep. 15, 1993 (Sep. 15, 1993), pp. 2516-2521.

International Search Report and Written Opinion for PCT/US2014/038421, ISA/EP Rijswijk, NL, dated Nov. 24, 2014.

* cited by examiner

INTEGRATED FLUIDIC SYSTEM FOR GAS CHROMATOGRAPHY

CROSS-REFERENCE TO RELATED APPLICATIONS

This application claims the benefit of U.S. Provisional Application No. 61/824,573, filed on May 17, 2013. The entire disclosure of the above application is incorporated herein by reference.

GOVERNMENT CLAUSE

This invention was made with government support under grant number W31P4Q-09-01-0011 awarded by the Army/AMC. The government has certain rights in this invention.

FIELD

The present disclosure relates to an integrated fluidic system for gas chromatography and fabrication techniques for the same.

BACKGROUND

A gas chromatograph (GC) is an instrument used to spatiotemporally separate and detect gas phase mixtures by passing sample plugs through a channel (i.e., the column) coated with a functional material (i.e., the stationary phase). The constituents can be identified by the time taken to elute from the column and quantified by the strength of the signal from a gas detector located downstream of the column. In general, many other components are also integral to the operation, such as the preconcentrator that provides sample injection and the pump that generates the gas flow. In some systems, valves are used to control the timing and direction of the flow. The separation of complex mixtures is sometimes performed using comprehensive two-dimensional GC (2DGC or GC×GC), in which a thermal modulator is used.

Since the widespread adoption of the gas chromatograph by the petroleum industry in the 1950s, its use has been extended to a number of other fields. For example, it is used to examine pollutants, such as polycyclic aromatic hydrocarbons, pesticides, halogenated compounds, etc. Another application is food analysis: coupled with the solid-phase microextraction technique, it is used for the identification and quantification of lipids, drugs, pesticides and carbohydrates. In recent years, biomedical screening has also been performed by this instrument. The analysis of human exhaled biomarkers by the GC provides a non-invasive approach for diagnosis and monitoring of potential diseases. Examples of such biomarkers include nitric oxide related to pulmonary inflammation, and ethane and pentane related to lipid peroxidation.

The miniaturization of the GC has been an ongoing effort for over 30 years, with early work dating back to 1979. As the core component of a micro gas chromatography (µGC) system, the separation column has been widely investigated and various column structures have been reported, such as the nickel column, the silicon-glass column, the Parylene™ column and the plasma-enhanced chemical vapor deposition (PECVD) oxynitride column. The stationary phase coating methods for these columns include the conventional static coating method as well as a self-assembly process. The gas injection device for a µGC system can be mainly classified into two categories: the preconcentrator and the valve injector. The preconcentrator uses sorbents to collect analytes at low temperatures and inject a plug with a thermal pulse. Certain preconcentrators collect analytes without the need for gas flow. Conversely, the valve injector utilizes valves to sample and inject a plug of gas. A variety of gas detectors have been reported, including the chemiresistor, the chemicapacitor, the thermal conductivity detector, the Fabry-Perot detector, and the discharge-based detector. A microfabricated thermal modulator has also been reported along with its application in a GC×GC system.

The integration of the microfabricated components into a µGC system has also made remarkable progress. The µChemLab is a hand-held µGC system that consists of a preconcentrator, a column, and surface acoustic wave sensors. Researchers at the University of Michigan have reported several prototypes of µGC over the past decade, including the Intrepid, the Spiron and the palm-size Mercury system.

Most µGC research efforts have not incorporated the use of micropumps. Only two cases have been reported: one with a microfabricated, electrostatically-actuated peristaltic pump and another with any array of motionless Knudsen pumps. The former required high frequency, large amplitude, drive voltages but was power-efficient. The latter was not power-efficient, but required only a low-voltage DC source; it provided high reliability, with continuous operation over 6000 hours.

Many micropump-operated µGC systems reported to date have used components fabricated by disparate microfabrication processes. Some systems connect the components by tubing, whereas some use manifolds for fluidic interconnect. The benefit of this approach is that each component can be optimally designed and fabricated. Unfortunately, the increased complexity and cost of the fabrication of the whole system pose a challenge for integration. As in other fluidic systems, a stackable architecture or a monolithic process for all of the components would greatly benefit the manufacturability and integration of the system.

This section provides background information related to the present disclosure which is not necessarily prior art.

SUMMARY

This section provides a general summary of the disclosure, and is not a comprehensive disclosure of its full scope or all of its features.

A method is presented for fabricating a fluidic system for a gas chromatograph. The method includes: microfabricating a portion of a fluidic system of a gas chromatograph on a substrate using a first mask; microfabricating a portion of the fluidic system of the gas chromatograph using a second mask; and microfabricating a portion of the fluidic system of the gas chromatograph using a third mask, such that the first mask, the second mask and the third mask are different from each other and the microfabricating of the fluidic system of the gas chromatograph is completed using only the first, second and third masks.

Microfabrication of the fluidic system typically requires patterned removal of material from the substrate by a step generally known as micromachining. Micromachining may be understood to be one of sandblasting, plasma etching, wet etching and ultrasonic machining. In some embodiments, the first mask is used to deposit a metal on the substrate, the second mask is used to form a cavity in the substrate and the third mask is used to form a through hole in the substrate.

The method may further include: microfabricating three components of the gas chromatograph on separate portions of the substrate; dicing the substrate into multiple dies, each die having a different sub-assembly for one of the three components disposed on each die; and stacking the multiple dies to form the gas chromatograph.

In some embodiments, fluidic system includes at least one of a pump, a separation column, a preconcentrator, and a detector being fabricated using only the first, second and third masks; whereas, in other embodiments, the pump, the separation column, the preconcentrator, and the detector are all fabricated using only the first, second and third masks.

Fabrication of the components of the fluidic system may be divided amongst two or more substrates. For example, metal may be deposited on a first substrate and sandblasting may occur on a second substrate. The first substrate is then assembled with the second substrate to form at least one of the pump, the separation column, the preconcentrator, and the detector. Lastly, the pump, the separation column, the preconcentrator and the detector may be assembled separately before being placed adjacent to each other on a circuit board.

A gas chromatograph system is also presented. The gas chromatography system includes: a pump configured to receive a carrier gas; a separation column configured to receive the carrier gas from the pump and operable to separate analyte molecules from the carrier gas; a preconcentrator interposed and fluidly coupled between the pump and the separation column; and a detector configured to receive the carrier gas from the separation column, wherein at least three of the pump, the separation column, the preconcentrator and the detector are fabricated by microfabricating using only three different masks.

In one embodiment, the gas chromatograph system has a stacked arrangement, where the preconcentrator is stacked on top of a Knudsen pump, the separation column is stacked on top of the preconcentrator, and the detector is stacked on top of the separation column.

In some embodiments, the Knudsen pump operates in one direction to draw the carrier gas into the preconcentrator and in a second direction to draw gas out of the preconcentrator.

In other embodiments, the detector is further defined as one of a pulse discharge detector or a capacitive detector, wherein the capacitive detector includes a channel through which the carrier gas passes and at least one interdigitated capacitor exposed in the channel.

In yet other embodiments, the gas chromatograph system has a planar arrangement, wherein the pump is comprised of two or more pumps disposed adjacent to each other on a circuit board to form a pump module, and the preconcentrator, the separation column and the detector are disposed adjacent to one another on the circuit board to form a chromatography module. At least one of the preconcentrator, the separation column and the detector can be arranged as a cantilever on a vertical support placed in between the circuit board and the at least one of the preconcentrator, the separation column and the detector.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Figure 1:
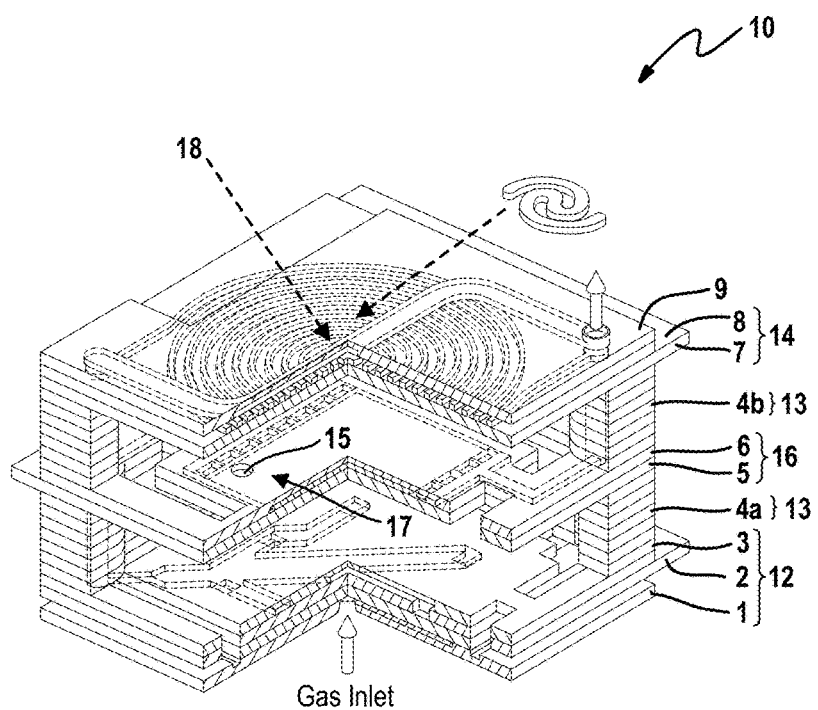
FIG. 1 is a perspective view of an example embodiment of a gas chromatography system.

FIG. 1 illustrates an example embodiment of a gas chromatograph system 10 having a stacked arrangement. The gas chromatography system 10 is comprised of a Knudsen pump 12, a separation column 14, a preconcentrator 16; and a detector 18. Each of these components are further described below. While the most relevant components are being described herein, it is envisioned that other types of components (e.g., a heat sink) may be used to implement a gas chromatograph system.

During operation, the Knudsen pump 12 operates on the principle of thermal transpiration to drive a gas of interest (i.e., carrier gas) through the system. The separation column 14 is configured to receive the gas of interest from the Knudsen pump 12 and operates to separate analyte molecules from the gas. The preconcentrator 16 adsorbs the analyte molecules prior to analysis by the separation column 14. To initiate analysis, the sample is desorbed with a thermal pulse and injected into the fluidic path. The detector 18 receives the sample from the separation column 14 and operates to quantify select species in the sample. In some embodiments, each component of the gas chromatograph is fabricated by micromachining using only three different masks as will be further described below.

Knudsen pumps are driven by thermal transpiration in narrow channels that constrain flow to the free-molecular or transition flow regimes. Gas molecules move against a temperature gradient, i.e., from the cold end to the hot end of the channels; the pump itself has no moving parts. In an example embodiment, the Knudsen pump 12 consists of three glass dies (Die 1-3, thickness=500 µm) sandwiching a stack of nanoporous mixed cellulose ester (MCE) membranes 8 (thickness≈105 µm, pore diameter≈25 nm, porosity≈70% Millipore, Mass.). The membranes are cut to 1.2× 1.2 cm² squares, which form the active pumping areas. The pore diameter is on the same order of magnitude as the mean free path of air near atmospheric pressure. Multiple grooves on Die 1 and multiple through-holes on Die 2 facilitate the gas flow through the MCE membrane, while the grooves on Die 3 guide the gas flow into the upper components. The temperature gradient is applied by a thin-film heater 9 on Die 2 and an external heat sink attached to the bottom of Die 1. In one embodiment, the heat sink is a simple aluminum plate with a perforation at the gas inlet. Its footprint may be slightly larger than the Knudsen pump.

Because of its computational ease and relative accuracy, Sharipov's model is often used for estimating the thermal transpiration phenomenon in microfabricated Knudsen pumps, which typically have long and convoluted channels. The thermal transpiration driven mass flow in a channel of circular cross section is provided by $$M_{avg} = \left[Q_T \frac{\Delta T_{KP}}{T_{avg}} - Q_p \frac{\Delta P_{KP}}{P_{avg}}\right] \frac{\pi a^3 P_{avg}}{l} \left[\frac{m}{2k_B T_{avg}}\right]^{\frac{1}{2}} \quad (1)$$

where $\Delta T_{KP}$, $\Delta P_{KP}$, $T_{avg}$ and $P_{avg}$ are the temperature difference, pressure difference, average temperature and average pressure between the hot end and the cold end of the channel, respectively, a is the channel radius, l is the channel length, m is the mass of the gas molecule, and $k_B$ is the Boltzmann constant. The parameters $Q_T$ and $Q_P$ are, respectively, the temperature and pressure flow coefficients, which were tabulated by Sharipov. The values of these coefficients depend on the rarefaction parameter, $\delta_{avg}$, which is given by:

$$\delta_{avg} = \frac{\sqrt{\pi}}{2} \frac{a}{\lambda_{avg}} \quad (2)$$

where $\lambda_{avg}$ is the mean free path of the gas molecule.

The volumetric flow rate of a Knudsen pump with numerous parallel channels can be calculated as:

$$Q_{KP} = \frac{M_{avg} \cdot N_{channel}}{\rho_{gas}} \quad (3)$$

where $N_{channel}$ is the total number of channels for thermal transpiration and $\rho_{gas}$ is the density of the gas.

Based on equations (1)-(3), the Knudsen pump described for this embodiment is estimated to provide 6.7 sccm unloaded air flow rate with $\Delta T_{KP}$=60° C. Its blocking pressure, the maximum $\Delta P_{KP}$, is estimated to be 6.7 kPa [by; letting $M_{avg}$=0 in equation (1)]. It is understood that the pump can be design for other air flow rates. It is also envisioned that other arrangements and/or types of pumps also fall within the broader aspects of this disclosure.

The preconcentrator 16 adsorbs the analyte molecules onto a porous surface at room temperature. To initiate analysis, sample is desorbed with a thermal pulse and injected into the fluidic path. The example embodiment utilizes a single bed preconcentrator, designed as 11 mm³ chamber 17 formed by Die 5 and Die 6 (see FIG. 1). Granules of Carbograph™2 (Grace Davison Discovery Sciences, IL), a graphitized carbon with a surface area of 10 m²/g, are packed in the chamber 17 as the sorbent material. In addition to the gas inlet and outlet features, the preconcentrator 16 contains a sorbent loading port 15 from which the sorbent granules can be loaded. The arrays of pillars are designed to confine the sorbent granules in the chamber 17. Other types of sorbent materials are contemplated by this disclosure.

The theoretical modeling of the sorbent-packed preconcentrators is often described using the Wheeler-Jonas model. The breakthrough time $t_b$ (min.) is a metric for characterizing the adsorption capability. Specifically, it is the time required for vapor that enters the preconcentrator 16 to saturate and reach a certain concentration at outlet (expressed as a fraction of that at inlet):

$$t_b = \frac{W_e}{Q \cdot c_{in}}\left[W - \frac{Q \cdot \rho_b}{k_v} \ln\left(\frac{c_{in}}{c_{out}}\right)\right] \quad (4)$$

where $W_e$ is the adsorption capacity that can be theoretically derived, W is the total sorbent mass (g), Q is the volumetric flow rate (cm³/min.), $c_{in}$ is the inlet chemical concentration (g/cm³), $\rho_b$ is the bulk density of the packed sorbent (g/cm³), $k_v$ is the overall mass transfer coefficient (min.⁻¹) that can be estimated from semi-empirical equations, and $c_{out}$ is the outlet chemical concentration chosen to denote breakthrough (g/cm³).

The preconcentrator 16 is designed to have the largest achievable sorbent chamber 17 without compromising the thermal isolation and form factor of the system (FIG. 1). As described below, $t_b$ is experimentally measured by setting $c_{in}$=80 ppm (determined by mole fraction of the sample vapor in the carrier gas used in this effort) and Q=1 sccm, while using a breakthrough criterion $$\frac{c_{out}}{c_{in}} = 10\%.$$

The column 14 separates analyte species as they pass along, based on the partition that each analyte establishes between the mobile phase (carrier gas) and the stationary phase. In the example embodiment, the column 14 is designed as a channel (length≈25 cm) laid out in a double-spiral pattern and formed by the bonding of Die 7 and Die 8 (FIG. 1). The manufacturing process creates an approximately semi-elliptical cross section (width≈300 µm, depth≈200 µm), which has a hydraulic diameter≈230 µm (defined as 4×area/perimeter). A≈0.2 µm thick non-polar polydimethylsiloxane (OV-1, Ohio Valley Specialty, OH) layer 19 is coated on the inner walls as the stationary phase. Other designs for a column also fall within the scope of this disclosure.

The separation efficiency of a chromatography column can be evaluated from experimentally obtained chromatograms. Higher separation efficiency is denoted by higher number of plates, N, as well as smaller dimension of a theoretical plate, termed the "height equivalent to a theoretical plate (HETP)." The HETP can be theoretically estimated from the structural dimensions and physical properties of the column, although these are not always well known. The HETP of the column can be calculated accordingly, which facilitates the evaluation and comparison of columns with various lengths.

$$N = 5.54 \left(\frac{t_R}{W_{1/2}}\right)^2 \quad (5)$$

$$HETP = \frac{l_{column}}{N} \quad (6)$$

where $t_R$ is the retention time, $W_{1/2}$ is the width of the retention peak measured at half height, and $l_{column}$ is the length of the separation column. For this work, $l_{column}$ is ≈25 cm. The experimentally-determined values of $t_R$ and $W_{1/2}$ are described below, along with the resulting HETP.

In the example embodiment, the discharge-based gas detector 18 uses two metal electrodes to create localized microdischarges, which generate optical spectra indicating the presence of carbon atoms. Although RF-powered microdischarges and DC microdischarges are options, pulsed DC microdischarges are used because they consume low power, require a simple interface circuit, and offer an extended lifetime. As shown in FIG. 1, the electrodes for creating microdischarges, spaced 50 µm apart, are located on Die 8, while the groove structure of Die 9 guides the gas to pass over the detector 18. The optical signal is detected by a hand-held spectrometer (Model # USB 2000, Ocean Optics, FL), which is controlled by a laptop computer.

With continued reference to FIG. 1, the four components are arranged in a stack forming a serially connected gas flow path. Driven by the Knudsen pump 12 located upstream, the preconcentrator 16 accumulates analytes and desorbs them along the same gas flow direction. The desorbed gas analytes pass through the column 14 with characteristic retention times that are temporally resolved by the detector 18. Thermal crosstalk between the pump 12, preconcentrator 16, and separation column 14 is inhibited by glass spacers (Dies 4a and Dies 4b) and the cut-outs (voids) in each layer. Depending on the system requirements, more spacers can be added to the system to achieve superior thermal isolation.

The thermal behavior of the stacked assembly was modeled using finite element analysis (FEA), for example in COMSOL Multiphysics 4.2. The simulations were directed at modeling the temperature distributions of the system while the Knudsen pump 12 or the preconcentrator 16 is heated. In both cases, the simulated structure included 7 spacers both between the preconcentrator and the column as well as between the preconcentrator 16 and the Knudsen pump 12, mimicking the actual system used for experimental tests. The thermal conductance of the MCE membrane stack 8 in the Knudsen pump 12 was derived from an experimentally fitted equivalent value. The bottom of the Knudsen pump was assumed to be maintained at room temperature by an ideal heat sink. The system was surrounded by an air box with natural convective heat transfer to the ambient.

In the case where the preconcentrator 16 is heated, it is subject to a thermal pulse (12 W, 2 sec.) and reaches 170° C. Because of the thermal isolation offered by the spacers and the pulsed nature of the heating, the column 14 and the Knudsen pump 12 are only minimally affected.

In the case where the Knudsen pump 12 is operational, there is a 50° C. temperature difference across the MCE membrane stack with 1 W input power. The simulation shows that the maximum parasitic temperature rises, after reaching steady state in ≈400 seconds, are ≈18° C. in the preconcentrator 16 and ≈14° C. in the separation column 14. This thermal crosstalk, which exists during both vapor sampling and analytical separation, is small enough that the preconcentrator 16 and the column 14 remain functional. The exact thermal crosstalk depends on how the system is operated. For vapor sampling and separation times shorter than 400 seconds, the thermal crosstalk is smaller.

Figure 2A:
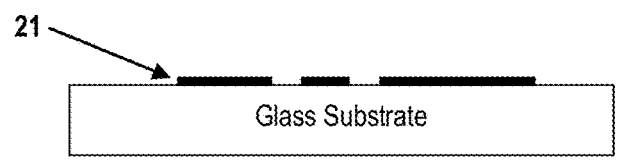
FIGS. 2A-2C are diagrams depicting a portion of the fabrication process.
Figure 2B:
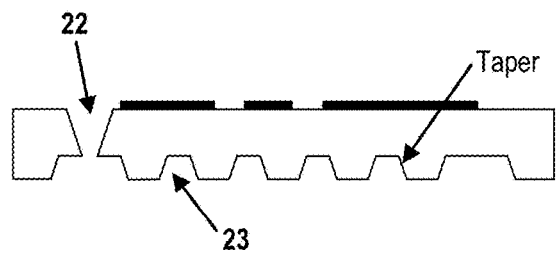
Figure 2C:
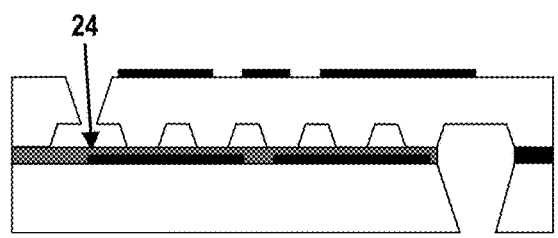

With reference to FIG. 2A-2C, the fabrication process can be divided into two major steps. The first is the lithographic microfabrication: a common 3-mask sequence is used for all four components of the gas chromatography system 10. The second is the assembly of the gas chromatography system 10.

The 3-mask sequence uses three mask-types: the first mask-type is intended for metallization on the substrate; the second mask-type is intended for creating grooves in the substrate; and the third mask-type is intended for creating through-substrate features (i.e., through holes and cutouts). The components (e.g., pump, preconcentrator, separation column, and detector) can be all fabricated on the same substrate or different combinations of the components can be fabricated on different substrates. In all cases, the three mask-types remain unchanged. Specifically, in one example, if all the components are fabricated on the same substrate, then each mask-type requires only one mask layout to incorporate the patterns of all the components. In another example, if the four components are each fabricated on a separate wafer, then each mask-type requires four separate mask design, each of which is used for patterning one of the components.

In an example fabrication process, borosilicate glass is selected as the substrate material in this effort. However, any other kind of glass, including the low-cost sodalime glass can be used. To start with, a metal layer 21 (e.g., Ti/Pt 25/100 nm) is deposited by e-beam evaporation and patterned by liftoff on a 500 µm thick glass wafer (see FIG. 2A), forming, for example heaters, temperature sensors and microdischarge electrodes. The metallized wafer is subject to a two-step machining process that grooves the non-metallized side of the wafer and creates through holes 22 and/or cutouts 23 (see FIG. 2B). Each of the microfabricating steps requires a mask. In the example process, a micro abrasive jet machining (sandblasting) was used (Bullen Ultrasonics, OH) although other methods are contemplated. The grooved structures form in-plane gas flow paths; and the through-wafer cutouts provide in-plane thermal isolation and stackable spacers. The sandblasted features typically have a 22° taper angle and a corner radius of 125 µm. In the example embodiment, the depth and feature sizes of the groove structures are in the range of 150-300 µm. In addition to sandblasting, many other approaches are available for micromachining glass wafers, such as plasma etching, wet etching and ultrasonic machining.

If each component is fabricated on a separate wafer, system assembly can be performed at the wafer level. In this example process, however, all the components are on the same wafer, so the dies are singulated prior to assembly.

Each of the components is then epoxy bonded to its upper layer before being added to the system stack as indicated at 24 of FIG. 2C.

In the example process, the Knudsen pump 12 is assembled into a glass-MCE-glass stack. Die 2 and Die 3 are first bonded by a low-viscosity epoxy Epotek 377 (Epoxy Technology, MA), which is applied from the perimeter of the dies that are arranged in a stack, and drawn into the seams between the mating surfaces by capillary force. Curing at 150° C. forms a leak free bond between the two glass dies. Next, Die 2, Die 3, four MCE membranes, and Die 1 are stacked (in order from top to bottom as stated). Finally a viscous epoxy Stycast2850FT (Henkel, Düsseldorf, Germany) is applied around the edge of the MCE membrane stack to achieve a hermetic seal, which is crucial to the operation of the Knudsen pump.

The preconcentrator 16 is assembled by epoxy bonding and sorbent packing. For example, Die 5 and Die 6 are bonded by Epotek 377. Next, sorbent granules are packed into the preconcentrator using a similar method to that described in J. H. Seo et al's, "Microfabricated Passive Vapor Preconcentrator/Injector Designed For Microscale Gas Chromatography". Moderate vacuum from the inlet/outlet is used to draw the Carbograph 2 granules from the loading port into the preconcentrator. The pillar structures in the preconcentrator act as sieves to contain larger particles while letting smaller particles to pass through and exit the preconcentrator. After sorbent loading, the loading port is sealed with either thermal tape or epoxy.

The separation column 14 is assembled by a coated layer, for example of SU-8 5 (MicroChem, MA). By way of example, Omnicoat (MicroChem, MA) is spin-coated and baked as the adhesion promotor, followed by a layer (less than 10 μm) of SU-8 spin-coated on the mating surfaces—specifically, the metallized side of Die 7 and the grooved side of Die 8. The grooved die (Die 8) is softbaked at 150° C. in order to prevent the potential problem of fluid SU-8 filling and blocking the channel. Then the dies are aligned and stacked, followed by a second softbake at 95° C., which drives the fluid SU-8 to gradually fill the gaps and voids between the mating surfaces, providing a leak free bond. The device is exposed to ultraviolet (UV) radiation and hardbaked at 150° C. to cure the SU-8 and minimize outgassing. The spin-coating process described above fully covers the inner walls of the separation column with SU-8, providing two potential benefits for obtaining a more uniform coating of stationary phase. First, the inner surface of the column is a homogeneous material that provides uniform adhesion strength to the stationary phase. Second, any surface roughness on the grooves that may result from the sandblasting is smoothened by the SU-8 layer.

The SU-8 bonded column is then coated with a ≈0.2 μm thick layer of OV-1 stationary phase using a conventional static coating method. In this example process, a solution of OV-1 is prepared by dissolving OV-1 and its cross-linking agent dicumyl peroxide in pentane and filled into the column. With one end of the column sealed, pentane is evaporated from the other end of the column by vacuum, leaving OV-1 coated on the inner walls of the column. After that, the column is heated at 150° C. overnight to fully remove the solvent as well as to perform cross-linking. This coating process can be assisted by capillary tubes temporarily attached to both ends of the column using the epoxy Stycast2850FT; the capillary connections can be easily detached by localized heat after the coating process.

Alternative methods can be used to apply the stationary phase in the separation column. For example, the constituent dies can be spray coated with the stationary phase and subsequently bonded. In some embodiments, the entire inner walls are coated with the stationary phase. In other embodiments, the stationary phase is not applied to the grooved inner walls but rather is applied only to the ungrooved surface. While this approach may compromise performance, it can significantly reduce manufacturing costs.

The detector is assembled by bonding Die 9 to Die 8 with Epotek 377 using the process as described for assembling the Knudsen pump.

Figure 3:
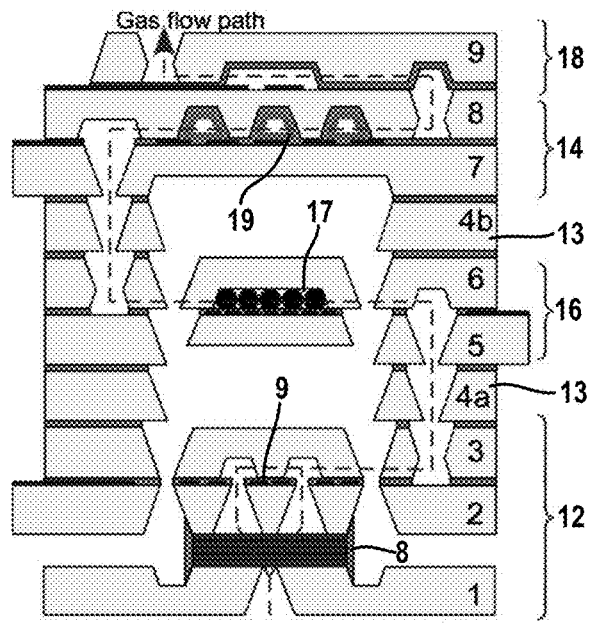
FIG. 3 is a cross-sectional view of the example embodiment of the gas chromatography system.

The overall system is finally integrated by the assembly of all four components together with a number of spacers, which are micromachined by sandblasting on the same glass wafer as the other dies as shown in FIG. 3. The spacers can be permanently bonded to the components using Epotek 377. However, a removable bonding layer between the components is also favored to allow reconfigurability. With low melting points and easy solubility in common solvents, various kinds of mounting wax have been widely used as temporary adhesives in the industry. The mounting wax QuickStick™135 (Electron Microscopy Sciences, PA) is used in this effort to provide the removable bonding layers. When assembling the system, the components are placed on a hot plate at 150° C. The mounting wax is melted by the elevated temperature and applied to the mating surfaces. The components are then pressed together, allowing the mounting wax to form a leak free bond. The thermal operation of the system does not damage this bond as long as no strong shear force is applied. When it is necessary to reconfigure the system, the stack can be heated on a hot plate and the bond can be easily detached.

The bottom surface of the stack can be attached to an aluminum plate, which serves as a heat sink for the Knudsen pump. Capillary tubes can also be attached to the inlet and outlet of the system for testing. The system has a footprint of 3.2 $cm^2$ and a height dependent on the number of spacers in the stack; a typical system tested in this effort has 14 spacers in total, corresponding to a total height of ≈1.15 cm and a form factor of 3.7 $cm^3$. While reference has been made to particular fabrication steps, it is readily understood that variations in the microfabricating steps or the order thereof, the bonding materials, etc. fall within the broader aspects of this disclosure.

Prior to the assembly of the full gas chromatography system 10, each component was separately evaluated. The experimental evaluations focused on alkanes in the range of $C_5$-$C_8$ for simplicity and benchmarking purposes. These alkanes are also indicative of the system response to typical indoor pollutants. The results are presented below.

Figure 4:
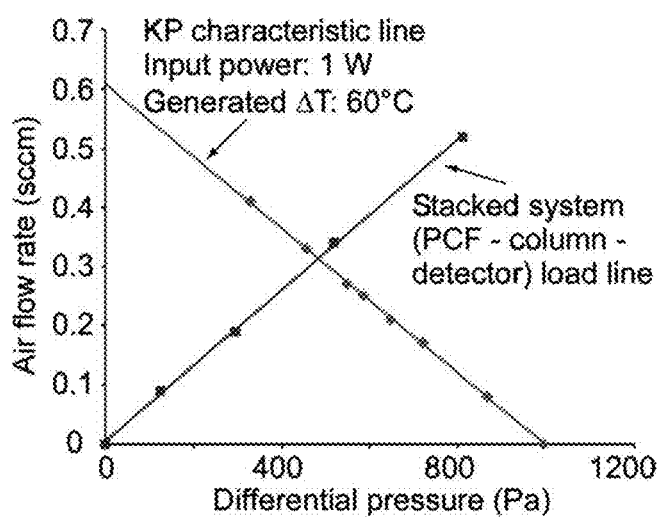
FIG. 4 is a graph illustrating the steady state performance of the Knudsen pump and the gas flow of the system.

In the evaluation of the Knudsen pump, its inlet was exposed to the ambient at atmospheric pressure, while varying loads (manifested as capillary tubes with varying length) were connected to its outlet. The values of the loads were selected to span over a wide range covering the actual load provided by the system. A commercial pressure sensor (Model # MPX5010DP, Freescale Semiconductor, AZ) and a flow meter (Part # FMA-1603A, Omega Engineering, CT) were connected between the outlet and the capillaries to monitor the pressure and flow conditions, respectively. With 1 W input power, the pump generated a $\Delta T_{KP}$ of ≈60° C., and was able to provide a steady state flow rate of 0.41 sccm against a pressure of 330 Pa; it provided a maximum pressure of 1 kPa. The flow rate declines linearly with load pressure as seen in FIG. 4. The deviation of experimental data from the theoretical estimates is likely due to imperfections in the MCE membranes or in the loss of a portion of the temperature gradient in the air gap between the heater and the membrane.

The load presented by the gas chromatography system 10 was measured using a similar setup. The only differences were: an external pump replaced the Knudsen pump and the component stack (including preconcentrator, column, and detector) replaced the capillary tubes. With the data points linearly fitted into a load line, the flow conductance of the stacked preconcentrator, column and detector can be read from the slope—0.64 sccm/kPa (see FIG. 4). The system operating point is indicated by the intersection between the Knudsen pump curve and the system load line.

The preconcentrator was characterized for both adsorption and desorption. The adsorption capability of the preconcentrator was experimentally evaluated by measuring the time taken by the vapor concentration at its outlet to reach a certain fraction of that at its inlet; this is known as "breakthrough." In this evaluation effort, the inlet of the preconcentrator was connected to a 2 L dilution bottle (Sigma Aldrich, WI) containing 80 ppm heptane in $N_2$; the vapor was drawn by a vacuum pump to pass through the preconcentrator at 1 sccm flow rate; the vapor concentration at the outlet was routed through a six-port valve to a flame ionization detector (FID) within a commercial Agilent 6890 GC. At two-minute intervals, the valve routed a fixed volume (100 μL) of the vapor downstream of the preconcentrator into the FID.

Figure 5A:
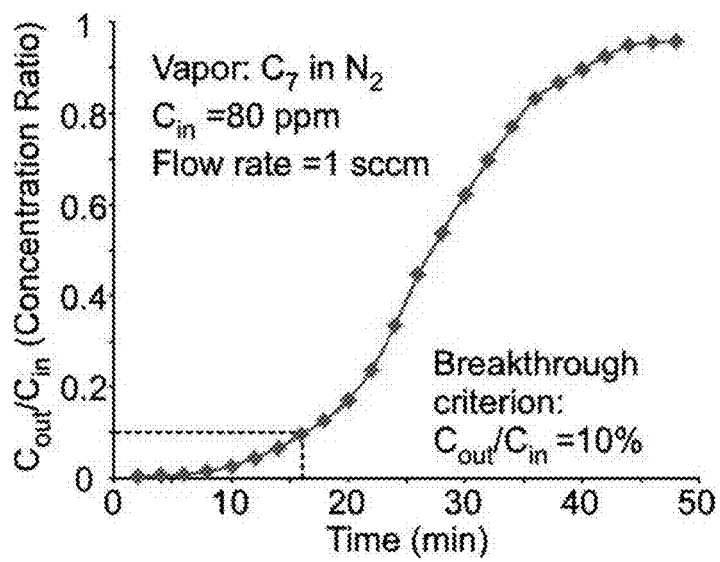
FIGS. 5A and 5B are graphs illustrating the evaluation of the performance of the preconcentrator.

In FIG. 5A, the heptane concentration at the preconcentrator outlet is normalized to that at its inlet. The preconcentrator saturated after 45 minutes of sampling and the heptane concentration at its outlet approached the concentration at its inlet. Conventionally, the breakthrough criterion is defined to be the outlet concentration at 10% of that at the inlet. For this work, this value corresponds to a breakthrough time of 16 minutes and a breakthrough volume of 16 mL for heptane.

Figure 5B:
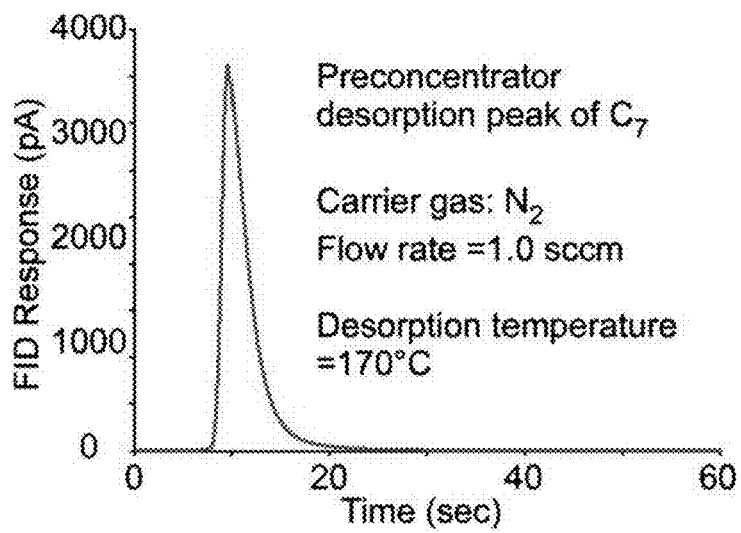

The thermal desorption of the preconcentrator was evaluated by the desorption peak in the chromatogram. The preconcentrator was first used to sample the heptane vapor and then connected to the Agilent 6890 GC where it was positioned upstream of the FID and downstream of the injection port. The desorption was performed by applying a pulse using the integrated thin-film heater, which heated the preconcentrator to 170° C. in 2 sec. The carrier gas was $N_2$ at a flow rate of 1 sccm; flow direction in the preconcentrator was the same during both sampling and desorption. As shown in FIG. 5B, a 1.4 sec desorption peak (measured at half height of the peak) is observed from the FID chromatogram with only minimal tailing. A second thermal pulse did not provide any additional desorption peak, verifying full desorption during the first thermal pulse. This characterization of the preconcentrator is a representation of its general capability rather than its actual performance with the system. This is because the gas chromatography system is operated at a lower flow rate of ≈0.2 sccm. Not only is this more easily accommodated by the pump, but the performance of the separation column is better at this flow rate.

Figure 6A:
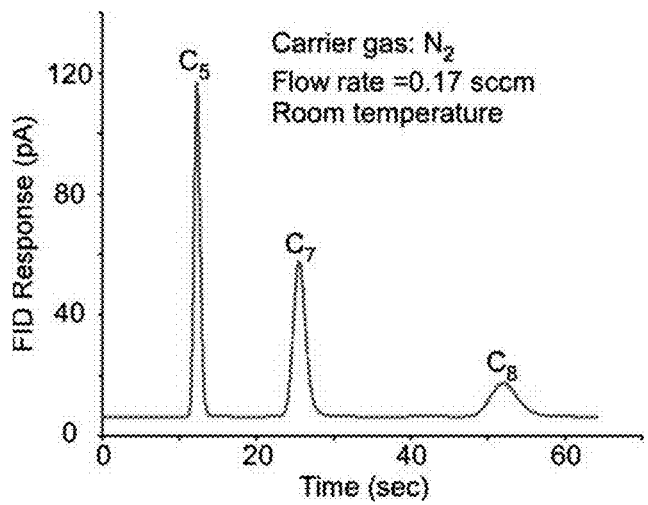
FIGS. 6A-6C are graphs illustrating the testing and evaluation results of the separation column.
Figure 6B:
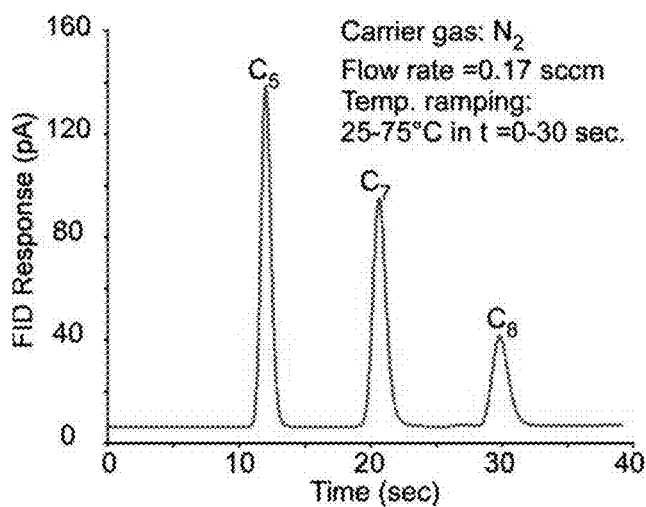
Figure 6C:
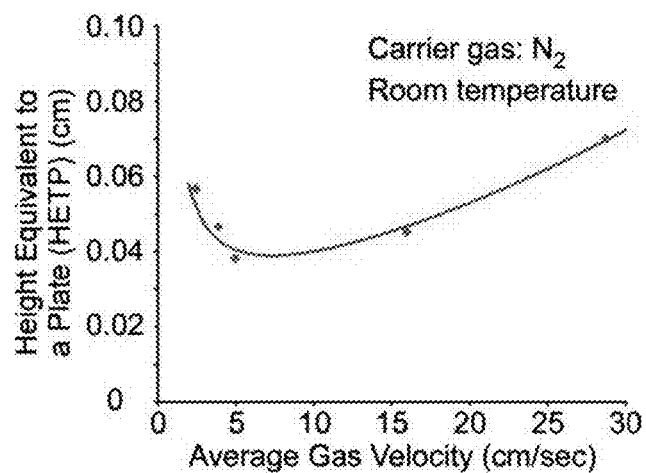

The separation column was evaluated by an Agilent 6890 GC system by positioning it downstream of an injection port and upstream of an FID. Sample chromatograms obtained with the tested column are shown in FIG. 6A-6C. At room temperature, three alkane species ($C_5$, $C_7$, and $C_8$) were separated by the column in about 52 seconds [FIG. 6A]. With a 30 sec.-long linear ramping of temperature from 25° C. to 75° C. provided by the on-chip heater, the column separated the same alkane mixture with the same gas flow rate in 30 sec. [FIG. 6B]. Both chromatograms were obtained using $N_2$ as the carrier gas at 0.17 sccm flow rate.

Golay plots are curves indicating how the column efficiency is affected by the carrier gas flow rate, which are helpful in determining the optimal operating point of the column. In this effort, a Golay plot was obtained by testing the separation column at room temperature for a number of $N_2$ carrier gas flow rates. The $C_8$ peak was used for calculating the number of plates N and the height-equivalent-to-a-plate HETP based on equations (5) and (6). As shown in FIG. 6C, the column has an optimal operating point at the gas velocity range of 5-10 cm/sec. (corresponding to the flow rate of 0.15-0.3 sccm), which gives HETP≈0.04 cm and a plate number (1/HETP) of ≈2600 plates/m. This performance is comparable to other microfabricated columns that have been previously reported—2000 plates/m, 3000 plates/m, and 4200 plates/m.

Figure 7A:
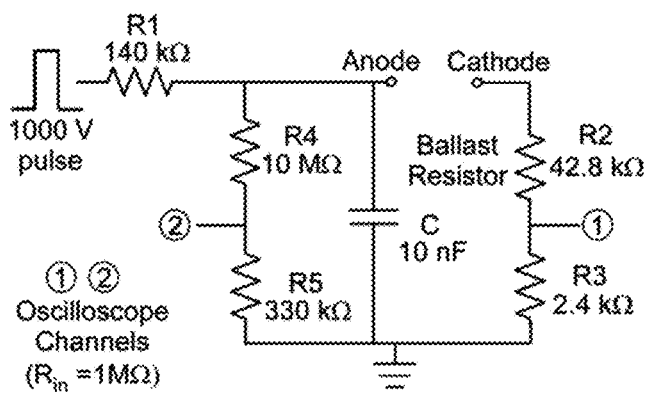
FIG. 7A is a schematic of an example discharge circuit for testing the detector.

The detector uses pulsed discharges that are controlled, for example by the circuit shown in FIG. 7A. In this circuit, the discharge energy is provided by capacitor C, which is charged by a single 1000-V pulse through R1. Once the anode reaches the breakdown voltage, which is typically ≈650 V, the discharge is initiated. Resistors R2 (the ballast resistor) and R3 are used to control the discharge current. The resistive dividers formed by R2/R3 and R4/R5 are connected to oscilloscope channels, so that the anode and cathode voltages as well as the discharge current can be observed.

Figure 7B:
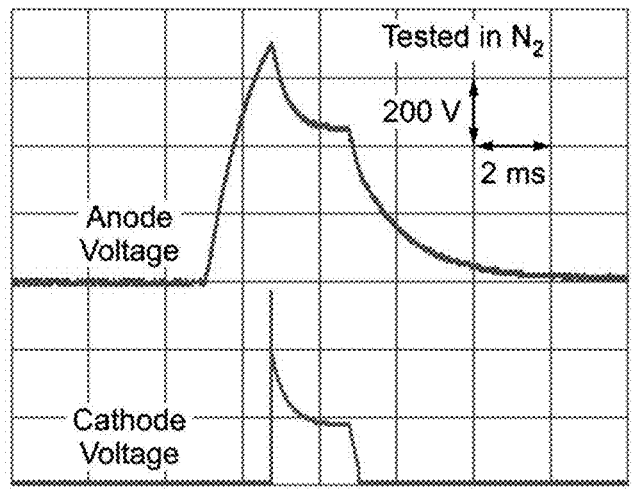
FIGS. 7B and 7C are graphs illustrating the testing and evaluation of the detector.

The typical transient voltages observed at the anode and cathode are shown in FIG. 7B. The anode took 1.6 ms to reach the breakdown voltage. The discharge current ran through the ballast resistor and raised the cathode voltage. Once initiated, the discharge presented in the circuit as 73 kΩ resistance. The high voltage pulse lasted 3.5 ms, during which the actual discharge took 1.9 ms. During the pulse, the typical energy consumed by the discharge was 2.9 mJ, while the total energy consumed by the whole circuit was 13.3 mJ.

Figure 7C:
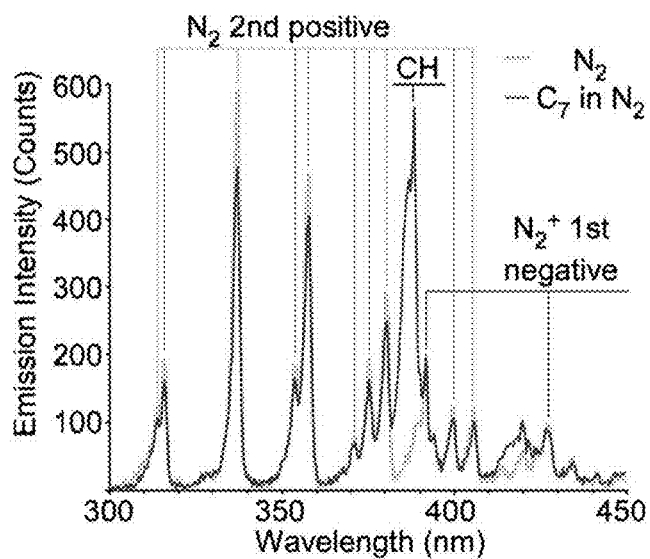

Optical emission from the microdischarge is guided by an optical fiber to a handheld spectrometer (Model # USB 2000, Ocean Optics, FL). The spectrometer uses a grating to diffract the incoming light. The resulting spatial distribution is captured by a charge-coupled device (CCD) array. The emission spectra, in the 300-450 nm window, of pure nitrogen and a heptane/nitrogen mixture are compared in FIG. 7C. The emission associated with the $N_2$ second positive system contains lines at 314 nm, 316 nm, 337 nm, 353 nm, 357 nm, 371 nm, 375 nm, 380 nm, 399 nm and 405 nm, while that associated with $N_2^+$ first negative system contains lines at 391 nm and 426 nm. With an elevated concentration of heptane, the emission spectrum shows a significant CH line at 387 nm. The intensity ratio of the CH line at 387 nm to the $N_2$ line at 337 nm was used as a measure of alkane strength to correct for possible variations in intensity from pulse to pulse. The data points with sufficient emission intensity (i.e., greater than 50 counts at 337 nm line) were used to construct chromatograms.

Figure 8A:
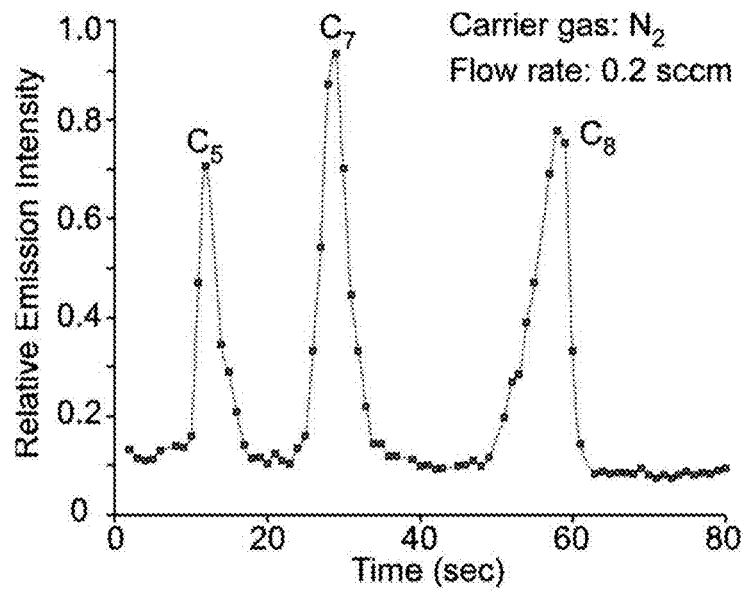
FIGS. 8A and 8B are graphs illustrating the separation of pentane, heptane and octane by the gas chromatography system.
Figure 8B:
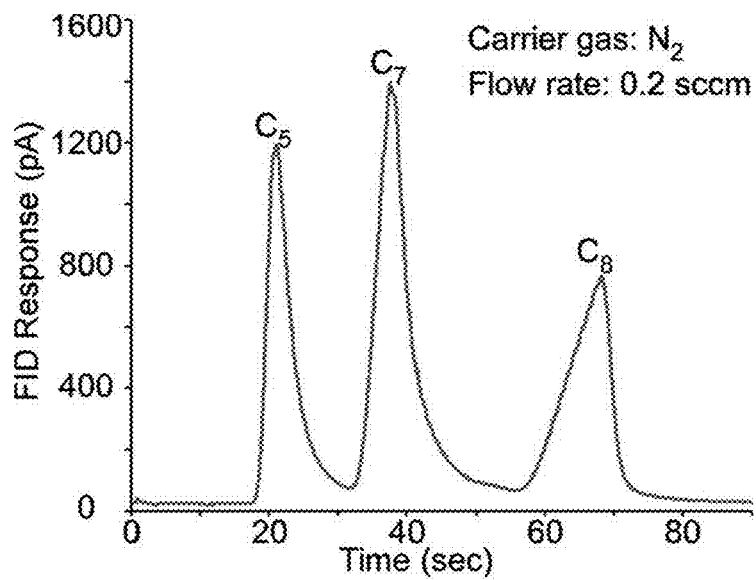

Typical chromatograms provided by the stacked gas chromatography system for alkane mixtures are shown in FIGS. 8A and 8B. FIG. 8A shows the data collected by the discharge-based detector. The three peaks correspond to the separation and detection of pentane, heptane and octane. FIG. 8B shows the benchmark FID response, verifying the results provided by the discharge-based detector. The FID signal lags behind that of the discharge-based detector as the FID is connected downstream of the stack. The relative peak heights among the three analytes are slightly different between the two chromatograms, possibly due to the emission characteristics of various species within the microdischarges. The power/energy consumption of the components and the gas chromatography system are summarized in Table I below. The run as shown had an average power consumption of 1.5 W.

TABLE I

POWER/ENERGY CONSUMPTION DURING THE iGC1 SEPARATION

| Component | Operation | Energy/Power | Comment |
|---|---|---|---|
| Knudsen pump | Steady state pumping | 1.1 W | Steady state power |
| Preconcentrator | 2 sec. thermal pulse | 34 J | Desorption energy |
| Column | Temperature programming | 1.06 W | Average power during ramping |
| Discharge-based detector | 3.5 ms high voltage pulse | 13.3 mJ/pulse | Energy per pulse |
| Stacked iGC1 system | Separation without column programming | 1.5 W | Average power during a run |

The results in FIG. 8A were obtained by first sampling a prepared vapor mixture. Driven by the integrated Knudsen pump, a mixture of pentane, heptane and octane in $N_2$ was sampled into the preconcentrator for ≈5 min. When initiating the separation, the preconcentrator was heated to 170° C. in 2 sec. to inject the vapor analytes into the column. The Knudsen pump was supplied with 1.1 W power, providing a $N_2$ flow rate of 0.2 sccm; the $N_2$ carrier gas was supplied by a Tedlar bag connected upstream of the system. Temperature programming of the separation column was not used in this experiment. The detector was created at 1 Hz (2 pulse/sec.) frequency. A customized LabVIEW® program was used to control the overall operation of the gas chromatography system.

Figure 9:
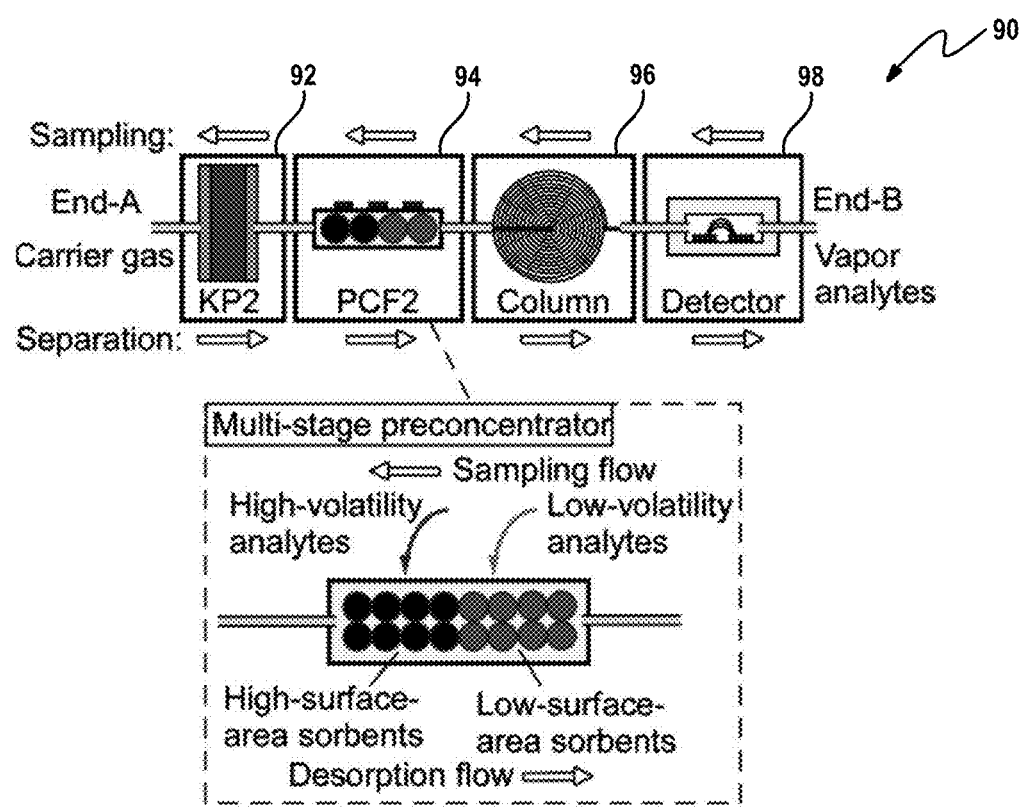
FIG. 9 is a diagram illustrating bi-directional operation of a gas chromatography system.

In a variant of the gas chromatography system described above, a bi-directional Knudsen pump may be used in place of the uni-directional Knudsen pump. FIG. 9 illustrates the bi-directional operation of a gas chromatography system 90 employing a bi-directional Knudsen pump 92. During the sampling phase, vapor analytes enter the system, pass through the detector 98 and column 96 and finally settle in the preconcentrator 94. In an example embodiment, the preconcentrator 94 employs a multi-stage design as will be further described below. During the analytical separation phase, the flow direction is reversed by the Knudsen pump 92. As a result, the sampled vapor analytes are thermally desorbed from the preconcentrator 94, separated by the column 96 and quantified by the detector 98.

Figure 10:
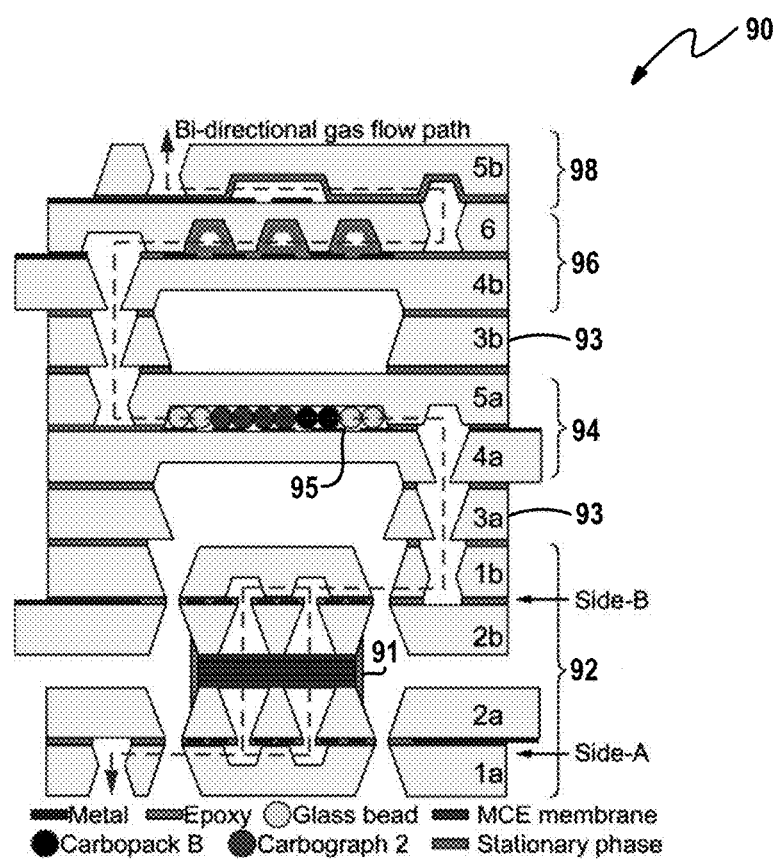
FIG. 10 is a cross-sectional view of an example embodiment of a gas chromatography system with a bi-directional Knudsen pump.

FIG. 10 further illustrates an example embodiment of the gas chromatography system 90 with a bi-directional Knudsen pump. The gas chromatograph system 90 is comprised of a Knudsen pump 92, a multi-stage preconcentrator 94, a separation column 96; and a detector 98. Each of these components is further described below.

In the example embodiment, the Knudsen pump 92 has a stack of four MCE membranes 91 sandwiched by two glass dies on each side, i.e., Side-A and Side-B. Each glass die is ≈500 μm thick. On Side-A, the glass die that is in contact with the MCE membrane stack (i.e., Die 2a) has a thin-film metal heater and thermistor to control the temperature, as well as multiple through-holes to facilitate gas flow into and out of the MCE membranes. The other glass die (i.e., Die 1a) has in-plane grooves that guide gas streams to a single port, which can be connected to other components or external test setup. The constituent glass dies on Side-B (i.e., Die 1b and Die 2b) are identical to Die 1a and Die 2a, respectively.

In the stack assembly (FIG. 2), Side-B is attached to the rest of the stack, whereas Side-A is attached to an external heat sink. During analytical separation, Side-B is heated while Side-A is cooled by the heat sink. During vapor sampling, Side-A (and the heat sink) is heated while Side-B is cooled by natural convection together with the rest of the stack.

Previously reported microfabricated multi-stage preconcentrators used multiple chambers, each containing one type of sorbent. In the gas chromatography system 90, however, the preconcentrator contains only one chamber designed in the shape of a channel; the two stages are formed by packing different sorbents in sequence. This design mimics its macro-scale counterpart: the multi-bed thermal desorption tube. It can be configured to include more than two stages without redesign.

More specifically, the preconcentrator 94 consists of a channel 95 (width≈1 mm, depth≈200 μm) formed by Die 4a and Die 5a (FIG. 10). The channel 95 is packed with four segments of particles in series: glass beads (with diameter 150-180 μm, Sigma Aldrich, WI); Carbograph 2 (with surface area≈10 m$^2$/g, diameter 120-150 μm, Grace Davison Discovery Sciences, IL); Carbopack B (with surface area≈100 m$^2$/g, diameter 112-140 μm, Sigma Aldrich, WI); glass beads (with diameter 150-180 μm, Sigma Aldrich, WI). The segment of Carbograph 2 is intended to trap vapors of lower volatility (e.g., toluene and xylene), and the segment of Carbopack B is intended to trap vapors of higher volatility (e.g., benzene). The two segments of glass beads, one at each end of the preconcentrator channel, are used to confine the two segments of sorbents in the central region of the device, where the temperature is the highest during thermal desorption. The preconcentrator 94 has advantages over prior preconcentrator designs because its narrower channel dimension provides less sensitivity to the non-uniformity of sorbent packing, as well as higher flow velocity at a given volumetric flow rate. In some embodiments, the design can be improved by incorporating pillar structures and sorbent loading port.

The separation column 96 is a channel (of length≈25 cm and hydraulic diameter≈230 μm) coated with a layer of ≈0.2 μm thick non-polar polydimethylsiloxane (PDMS or OV-1, Ohio Valley Specialty, OH) that serves as the stationary phase. The column is formed by Die 4b and Die 6 (FIG. 10). When passing along the separation column, vapor mixtures partition between the stationary phase material and the carrier gas. The non-polar PDMS stationary phase used in this work interacts with the vapor molecules mainly by van der Waals force. Vapor molecules with higher molecular weight typically have a stronger interaction with the stationary phase and display a longer retention time. Additionally, thicker coatings of the stationary phase provide a stronger interaction with the vapor molecules and extend retention times.

The gas detector 98 consists of two thin-film metal electrodes on a glass substrate (i.e., Die 6). In the example embodiment, the metal layer consists of Ti/Pt of thickness 25/100 nm. The two electrodes (i.e., anode and cathode) are spaced 50-200 μm apart. Electrodes of other materials, thickness, and separation can also be used. The groove in Die 5b forms the detector channel that guides gas flow over the electrodes (FIG. 10). By applying a voltage pulse between the two electrodes, a microdischarge is generated. The resulting optical intensity at the line that is specific to the C—H emission can be used to quantify carbon-containing species in the gas flow. In contrast to flame ionization detectors (FID) that are often used within commercial GC systems, microdischarge based detectors do not require a stored supply of H2 to create the ionization, and are more amenable to monolithic integration.

The Knudsen pump 92, the preconcentrator 94, the column 96 and the detector 98 are integrated in the form of a stack that also uses fourteen 500 μm-thick glass spacers 93 (Dies 3a and Dies 3b). The spacers 93 provide thermal isolation between adjacent components. Perforations in the spacers allow interlayer flow. The dashed line in FIG. 10 indicates the gas flow path of the system.

All four components as well as the spacers of the gas chromatography system 90 are fabricated on glass wafers using the same three-mask lithographic processes as described above in relation to gas chromatography system 10. Hence, these elements may be either fabricated on separate wafers or all on a single wafer. The use of glass as the substrate material has several benefits. It is lower in cost than silicon and ceramic options, and can be easily micromachined. In addition, the transparent nature of glass permits visual inspection of the interior of the devices, which benefits early stage research and development. Other variants to the components and the fabrication thereof discussed above are also applicable to the gas chromatography system 90 as well.

Various improvements are envisioned for the gas chromatography system 90. For example, a longer column can provide better separation of retention peaks, and heating of the column both during sampling and separation is likely to improve various aspects of the performance. In addition, the use of sorbents with higher surface area within the preconcentrator would permit analyses of vapors with lower concentrations. All these approaches are intended to analyze more complex vapor mixtures. Nonetheless, a more powerful micro gas pump may be required to maintain the gas flow rate in a longer column. This can be accomplished by a multistage Knudsen pump. Thus, the stackable architecture in this disclosure provides a simple and compact integration of the system, as well as the scalability to longer columns (by stacking multiple short columns).

Figure 11:
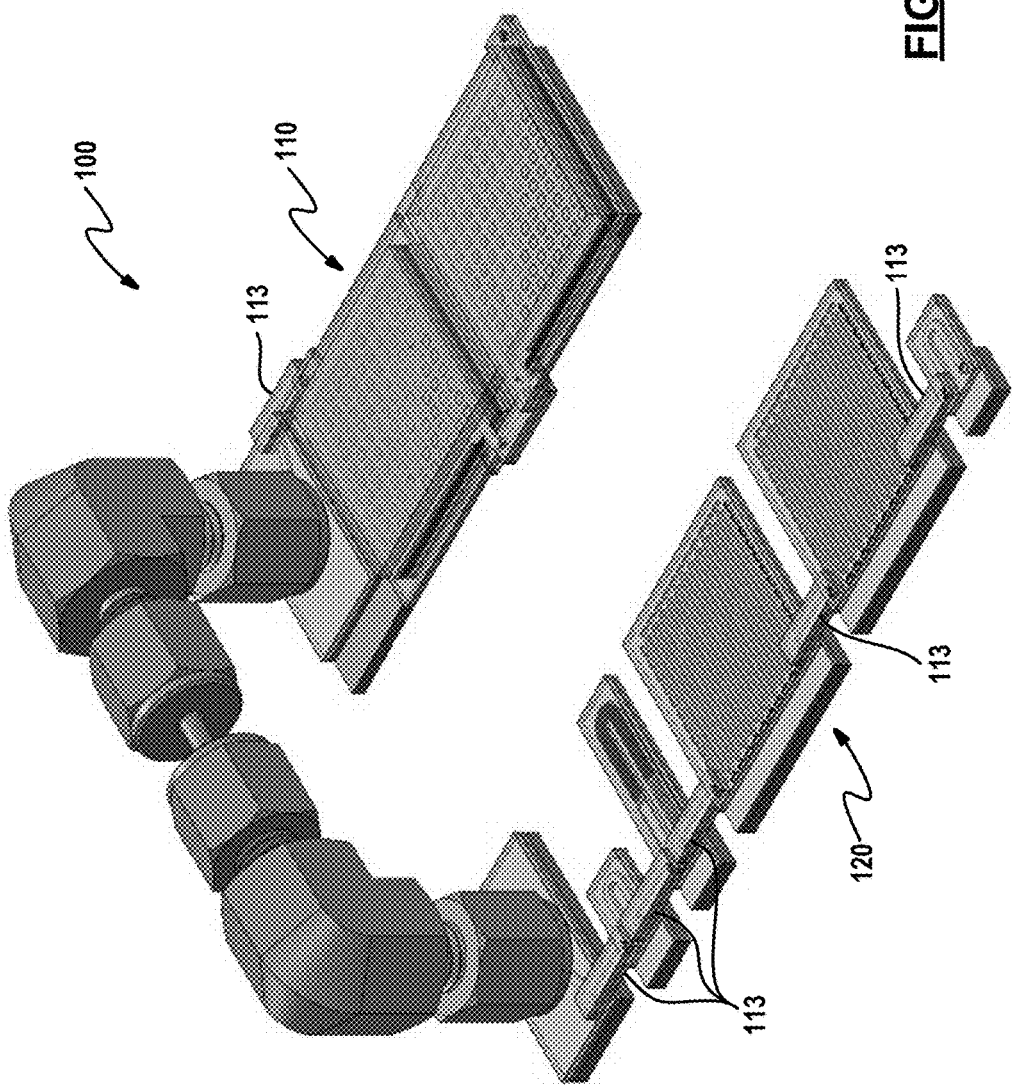
FIG. 11 is a diagram depicting another example embodiment of a gas chromatography system having a planar and modular design.

FIG. 11 illustrates another example embodiment of a gas chromatograph system 100. In this embodiment, the gas chromatograph system 100 is comprised of two planar modules: a pump module 110 and a chromatography module 120. Gas flow interconnects between components of a module are implemented by gas flow connectors 113 as will be further described below. Of note, the gas flow connectors 113 are fabricated using the same method as the other components associated with the module. Gas flow connections between the two modules are made, for example using flexible compression tubing.

Figure 12:
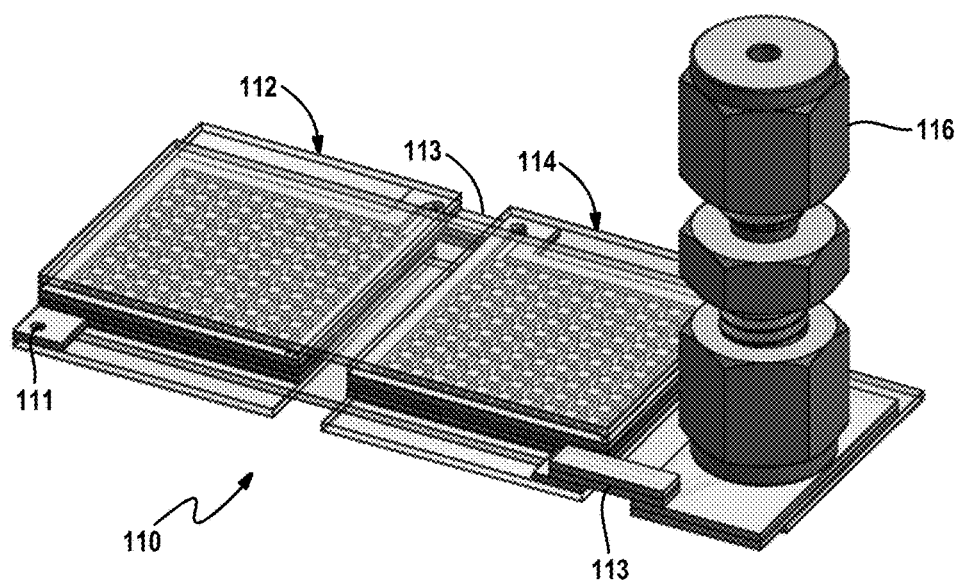
FIG. 12 is a perspective view of a pump module in the gas chromatography system of FIG. 11.

The pump module 110 is further described in relation to FIG. 12. In an example embodiment, the Knudsen pump (KP) module 110 is designed for providing higher pressure and flow to the chromatography module 120. In particular, a two-stage arrangement is shown having one Knudsen pump 112 positioned adjacent to a second Knudsen pump 114. It is envisioned that more stages can be added in either series or parallel to increase the pressure and flow rate as needed. A compression tube fitting 116 is disposed on one end of the module for connecting the pump arrangement to chromatography module 120. A particle filter can be implemented at a port 111 that serves as an inlet during the analytical separation. The filter blocks dust particles during normal operation. When analytical cycles are completed, the particles can be purged by elevated flow for a prescribed duration, which is generated by the bi-directional gas pump. The gas flow conductance of the filter can be increased by increasing the area of the filter, assuring a relatively small pressure drop across the filter and thereby reducing the gas flow loading to the pumps. In some embodiments, the filter is integrated into the housing/package for the system. Similarly, a moisture filter can be implemented at the port 111 that serves as an inlet during analytical separation. The moisture filter contains a channel that is coated with water-selective material, which retains water vapor at room temperature during analytical separation. When the analytical separation is completed, the retained water can be rapidly released by heating the moisture filter, and purged by the bi-directional pump with a reversed flow.

Figure 14:
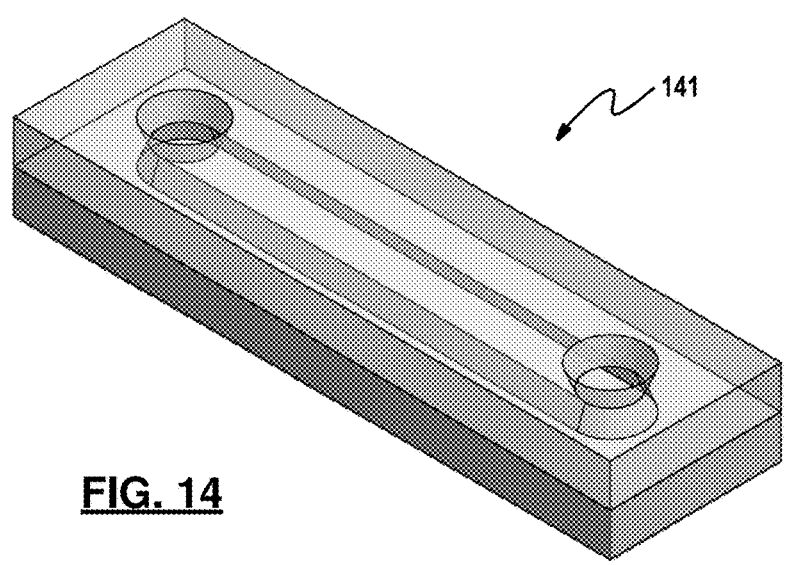
FIG. 14 is a perspective view on an example gas flow connector.

Gas flow connectors 113 are used to fluidly couple the pumps to each other as well as fluidly couple the second Knudsen pump 114 to a channel leading to the tub fitting 116. An example gas flow connector 141 is shown in FIG. 14. The gas flow connectors can be fabricated by the same method as the separation columns (i.e., by using the two-step sandblasting), or co-fabricated on the same wafer as other components of the pump module.

Figure 13A:
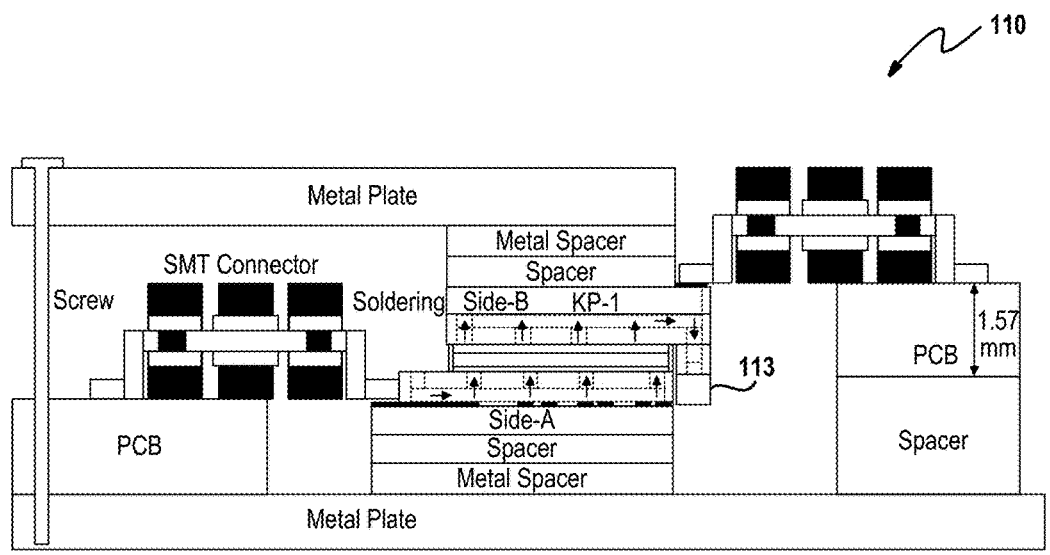
FIGS. 13A and 13B are cross-sectional views of the pump module.
Figure 13B:
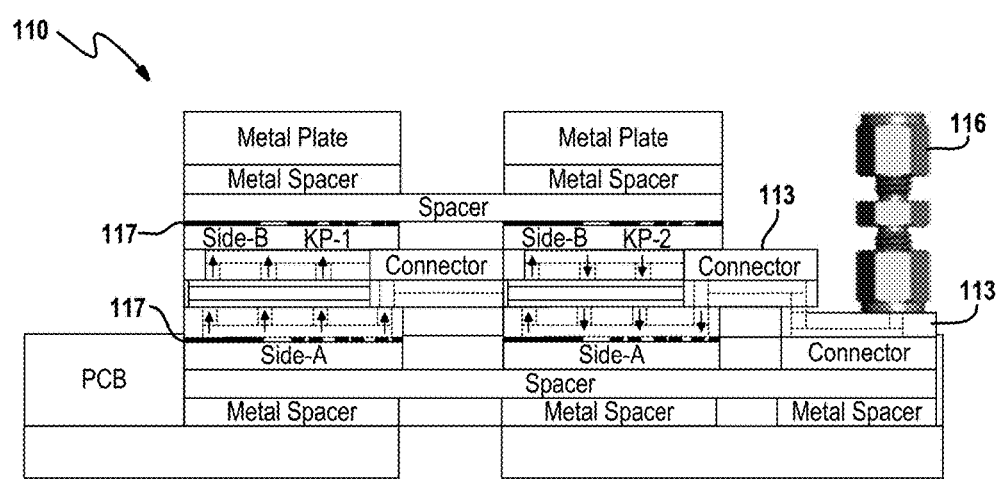

Construction of the two Knudsen pumps is further illustrated in FIGS. 13A and 13B. To provide bi-directional pumping, each KP stage has thin-film metal heaters (e.g., formed by metal plates as indicated at 117) as well as heat sinks integrated on both its top and bottom sides (Side-B and Side-A). The gas flow direction is in turn determined by which heater is used. Components of the pump module 110 are otherwise fabricated using the same three-mask lithographic processes as described above in relation to gas chromatography system 10.

Figure 15A:
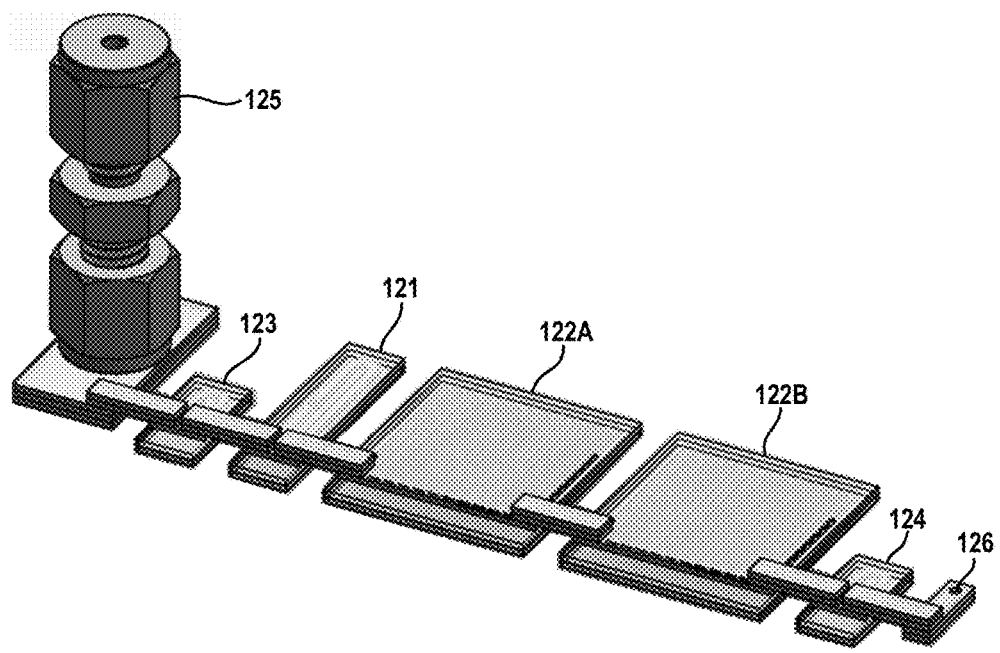
FIG. 15A is a perspective view of a chromatography module in the gas chromatography system of FIG. 11.
Figure 15B:
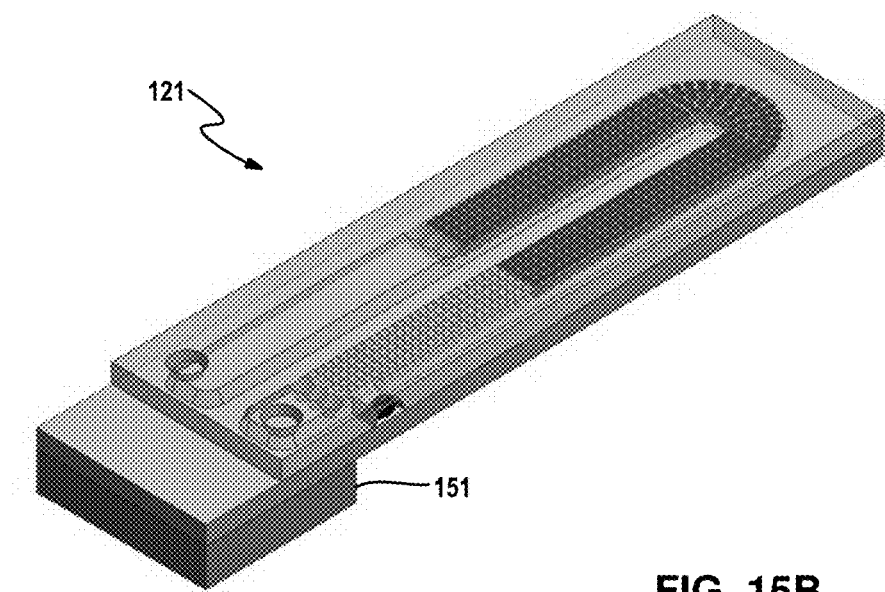
FIG. 15B is a perspective view of an example preconcentrator.

On the other hand, the chromatography module 120 is further described in relation to FIGS. 15A and 15B. The chromatography module 120 includes preconcentrator focuser (PCF) 121, separation columns 122A, 122B, and two detectors 123, 124. A compression tube fitting 125 is disposed at one end of the module adjacent to detector 123. A tube received at one end by the tube compression fitting 116 on the pump module 110 and at the other end by the compression fitting 125 on the chromatography module 120 interconnect the two modules. A particle filter can be implemented at a port 126 that serves as serves as an inlet during vapor sampling. The filter blocks dust particles during normal operation. When sampling is completed, the particles can be purged by elevated flow for a prescribed duration, which is generated by the bi-directional gas pump. Similarly, a moisture filter can be implemented at the port 126 that serves as an inlet during vapor sampling. The moisture filter contains a channel that is coated with water-selective material, which retains water vapor at room temperature during normal operation. When the vapor sampling is completed, the retained water can be rapidly released by heating the moisture filter, and purged by the bi-directional pump with a reversed flow.

During operation, the gas chromatograph system 100 uses the same bi-directional flow strategy as described above in relation to gas chromatography system 90. During vapor sampling, the vapor analytes enter the chromatography module 120 via the inlet 126, pass through the columns 122A, 122B, and get trapped by the preconcentrator focuser 121. During analytical separation, the gas flow direction is reversed. In sampling, low volatility vapors are held closer to PCF/column interface; whereas, high volatility vapors may penetrate further. In the analytical separation period, when flow is reversed, this distribution favors the release of all the constituent vapors in a narrow plug.

In some embodiments, the preconcentrator 121 may be arranged as a cantilever on a vertical support 151 as shown in FIG. 15B. That is the preconcentrator is elevated from an underlying platform (e.g., PCB) by a spacer, which only supports one end of the preconcentrator 121. The sorbent particles are located close to the other end of the preconcentrator, where the heated zone is located. This design feature relieves thermal stress and minimizes thermal loss without compromising the structural robustness. While this design feature is described in relation to the preconcentrator 121, it may be applied to other heated components, such as the separation columns and/or detectors.

Detector 123 serves as a reference and is disposed between the compression tub fitting 125 and the preconcentrator focuser 121. In principle, with the bi-directional flow, the vapor analytes never reaches the reference detector 123. By subtracting signals of the reference detector 123 from the signals of the primary detector 124, a differential signal can be generated with which the common-mode interference can be rejected. It is understood that the reference detector 123 may take on different forms but is constructed in the same manner as the primary detector 124.

Figure 16:
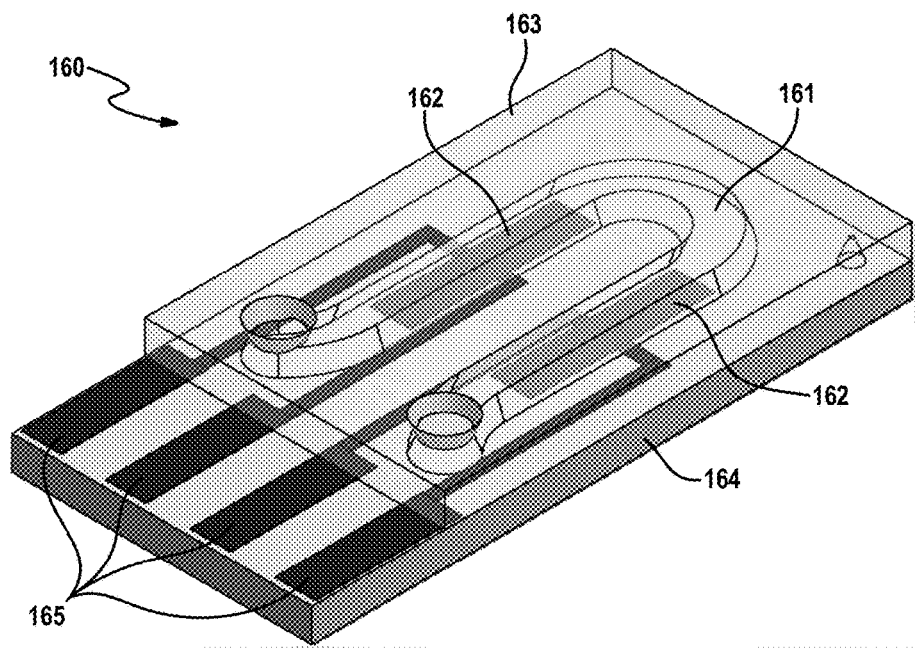
FIG. 16 is a perspective view of an example embodiment of a capacitive detector which may be used in a gas chromatography system.

FIG. 16 depicts an example embodiment for a capacitive detector 160. The capacitive detector is comprised generally of a gas flow channel 161 and at least one capacitor 162 residing in the gas flow channel. In an example embodiment, the gas flow channel 161 is formed by (or between) the bonding of a sandblasted die 163 and a metallized die 164. The capacitors 162 are formed on the metallized die. More specifically, a capacitor 162 having an interdigitated pattern is formed in each arm of a U-shaped channel. Each capacitor in turn has two leads or electrodes 165 which may be used to electrically couple the capacitors to the underlying circuit board. Other arrangements for capacitors inside of the channel are also contemplated by this disclosure.

Figure 17:
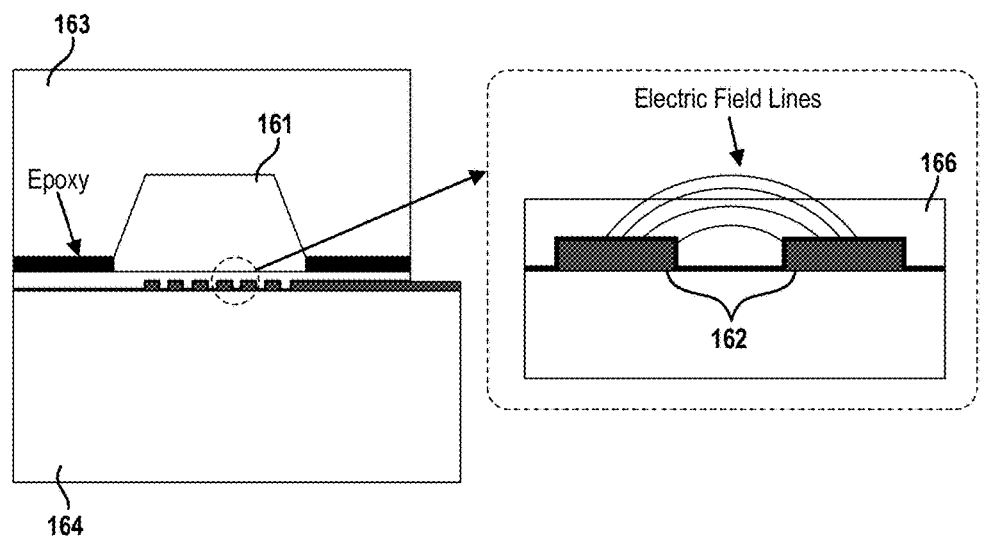
FIG. 17 is a cross-sectional view of the capacitive detector.

With reference to FIG. 17, a dielectric layer 166 can be used to coat the metal forming the capacitor to prevent electrical shorting between metal lines forming the pattern. In an example embodiment, the dielectric layer 166 is formed by a 10 nm thick aluminum oxide layer which is deposited by atomic layer deposition. Other dielectric materials and coating methods can be used. It can be appreciated that the dielectric coating is not necessary if the assembly process is performed in a clean environment.

To perform vapor sensing, a polymer layer 167 is coated on the metal pattern forming the capacitor. When a vapor passes over the metal pattern in the gas flow channel, a fraction of the vapor molecules diffuse into the polymer layer 167, causing a change in polymer thickness and/or dielectric constant. This changes the spatial distribution of electric field lines between the two metal lines, thereby changing the capacitance sensed by electrical interface. In an example embodiment, the polymer layer 167 is OV-1 (thickness 0.1-2 µm), which is the same polymer used in the separation column as the stationary phase. Other vapor-sensitive polymers can be used. In this example, the coating method of the OV-1 layer is spin-coating of an OV-1 solution (i.e., OV-1 dissolved in nonane) on the metallized die although other coating methods can also be used. While the capacitive detector 160 has been described in relation to the planar arrangement shown in FIG. 11, it is understood that a capacitive detector as applied to gas chromatography is unique and thus can be applied in other arrangements, such as the GC system shown in FIG. 1.

Fabrication of the gas chromatograph system 100 is similar to the methods used to fabricate the gas chromatography system 10. That is, components for the pump module 110 and the chromatography module 120 are fabricated on glass wafers using the three mask lithographic process described above. With the embodiment of the gas chromatography system 100, the fabrication process can be simplified from that for the gas chromatography system 10. The gas chromatography system 10 requires that each glass wafer is microfabricated using the entire three-mask lithographic process, so as to include features of metal, through-holes, and grooves. However, for the gas chromatography system 100, the three-mask lithographic process can be partially applied to different glass wafers, i.e., certain wafers are only micromachined using a two-mask lithographic process to include through-hole and groove features, whereas other wafers are only lithographically metallized using the third mask. Such a fabrication strategy allows concurrent fabrication of the wafers and reduces the risk in fabrication.

Dies for each component are then assembled together before being mounted to a common substrate, such as a printed circuit board. For example, the sandblasted die 163 is bonded to metalized die 164 to form a capacitive detector. Next, fluid connections are made between components as well as between the two modules. Lastly, electrical connections are made between the components and the printed circuit board. For example, electrical connections are made between the terminals of various heaters and the circuit board. Variants described for the fabrication process above are also applicable to gas chromatograph systems having a planar arrangement as shown in FIG. 11.

In a variant of the gas chromatography system 100, the fluidic system (i.e., pump, separation column, preconcentrator and detector) can be fabricated using only a two-mask lithographic process to form through-hole and groove features but without use of the third mask for metallization. Heating is then applied from elements which are external to the fluidic system.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

What is claimed is:

1. A gas chromatograph, comprising:
a detector having an inlet to receive a gas;
a separation column fluidly coupled to the detector and configured to receive the gas from the detector and operable to separate analyte molecules from the gas; and
a pump having an outlet;
a preconcentrator interposed and fluidly coupled between the pump and the separation column;
wherein the pump is arranged to operate in a first direction to draw the gas into the preconcentrator and in a second direction to push gas out of the preconcentrator, and at least three of the pump, the separation column, the preconcentrator and the detector is fabricated by a microfabricating method, wherein the preconcentrator, the separation column and the detector are fluidly connected together by gas flow connectors, such that the gas flow connectors are fabricated using same processes as in the microfabricating method used to fabricate the other components of the gas chromatograph.

2. The gas chromatograph of claim 1 wherein the pump is further defined is a Knudsen pump.

3. The gas chromatograph of claim 2 having a stacked arrangement, where the preconcentrator is stacked on top of the Knudsen pump, the separation column is stacked on top of the preconcentrator, and the detector is stacked on top of the separation column.

4. The gas chromatograph of claim 3 wherein the Knudsen pump is comprised of at least one nanoporous membrane sandwiched between glass dies.

5. The gas chromatograph of claim 4 further comprises a metal film integrated into dies to serve as heaters.

6. The gas chromatograph of claim 5 further comprises spacers interposed between the Knudsen pump and the preconcentrator, and spacers interposed between the preconcentrator and the separation column.

7. The gas chromatograph of claim 1 wherein the preconcentrator includes a chamber which the gas passes through and sorbent granules embedded in the chamber, where the chamber hosts sorbent granules of at least two types.

8. The gas chromatograph of claim 1 wherein the separation column includes a channel through which the gas passes and the channel has a serpentine pattern.

9. The gas chromatograph of claim 1 wherein the detector is further defined as one of a pulse discharge detector or a capacitive detector.

10. The gas chromatograph of claim 9 wherein the capacitive detector includes a channel through which the gas passes and at least one interdigitated capacitor exposed in the channel.

11. The gas chromatograph of claim 1 having a planar arrangement, wherein the pump is comprised of two or more pumps disposed adjacent to each other on a circuit board to form a pump module, and the preconcentrator, the separation column and the detector are disposed adjacent to one another on the circuit board to form a chromatography module.

12. The gas chromatograph of claim 11 wherein at least one of the preconcentrator, the separation column and the detector are arranged as a cantilever on a vertical support placed in between the circuit board and the at least one of the preconcentrator, the separation column and the detector.

13. The gas chromatograph of claim 11 further comprises a reference detector disposed between a port configured to receive the gas from the pump module and the preconcentrator.

14. The gas chromatography of claim 1 wherein during a sampling phase, vapor analytes enter the gas chromatograph, pass through the detector and the separation column and settle in the preconcentrator, and during an analytical separation phase, the flow direction is reversed by the pump, and the vapor analytes are thermally desorbed from the preconcentrator, separated by the separation column and quantified by the detector.

15. A gas chromatograph, comprising:
a detector having an inlet to receive a gas;
a separation column fluidly coupled to the detector and configured to receive the gas from the detector, the separation column operates to separate analyte molecules from the gas;
a pump having an outlet; and
a preconcentrator fluidly coupled between the pump and the separation column, where at least three of the pump, the separation column, the preconcentrator and the detector is fabricated by a microfabricating method;
wherein, during a sampling phase, the pump operates to draw the gas into the inlet of the detector, such that the gas passes through the separation column and into the preconcentrator and, during an analytic separation phase, the pump operates to reverse the flow of the gas, such that the gas moves from the preconcentrator through the separation column and into the detector.

16. The gas chromatograph of claim 15 wherein the pump is further defined is a Knudsen pump.

17. The gas chromatograph of claim 16 having a stacked arrangement, where the preconcentrator is stacked on top of the Knudsen pump, the separation column is stacked on top of the preconcentrator, and the detector is stacked on top of the separation column.

18. The gas chromatograph of claim 17 wherein the Knudsen pump is comprised of at least one nanoporous membrane sandwiched between glass dies.

19. The gas chromatograph of claim 18 further comprises a metal film integrated into dies to serve as heaters.

20. The gas chromatograph of claim 19 further comprises spacers interposed between the Knudsen pump and the preconcentrator, and spacers interposed between the preconcentrator and the separation column.

21. The gas chromatograph of claim 15 wherein the preconcentrator includes a chamber which the gas passes through and sorbent granules embedded in the chamber, where the chamber hosts sorbent granules of at least two types.

22. The gas chromatograph of claim 15 wherein the separation column includes a channel through which the gas passes and the channel has a serpentine pattern.

23. The gas chromatograph of claim 15 wherein the detector is further defined as one of a pulse discharge detector or a capacitive detector.

24. The gas chromatograph of claim 23 wherein the capacitive detector includes a channel through which the gas passes and at least one interdigitated capacitor exposed in the channel.

* * * * *